United States Patent
Koennecke

(10) Patent No.: US 7,303,279 B2
(45) Date of Patent: Dec. 4, 2007

(54) SYSTEM TO FACILITATE ALIGNMENT AND FOCUSSING OF A FUNDUS CAMERA

(75) Inventor: Greg Koennecke, Adelaide (AU)

(73) Assignee: Vision Instruments Pty Ltd, Adelaide (AU)

( * ) Notice: Subject to any disclaimer, the term of this patent is extended or adjusted under 35 U.S.C. 154(b) by 588 days.

(21) Appl. No.: 10/710,003

(22) Filed: Jun. 11, 2004

(65) Prior Publication Data

US 2005/0151928 A1    Jul. 14, 2005

Related U.S. Application Data

(63) Continuation of application No. PCT/AU02/01681, filed on Dec. 13, 2002.

(30) Foreign Application Priority Data

Dec. 13, 2001 (AU) .................................. PR9500

(51) Int. Cl.
*A61B 3/14* (2006.01)

(52) U.S. Cl. .................................................. 351/206

(58) Field of Classification Search ................. 351/206, 351/208, 211, 214, 220–221
See application file for complete search history.

(56) References Cited

U.S. PATENT DOCUMENTS

| | | |
|---|---|---|
| 4,252,420 A | 2/1981 | Kohayakawa |
| 5,152,295 A | 10/1992 | Kobayashi et al. |
| 5,568,208 A | 10/1996 | Van de Velde |
| 5,742,374 A | 4/1998 | Nanjo et al. |
| 5,751,396 A | 5/1998 | Masuda et al. |
| 6,361,167 B1 | 3/2002 | Su et al. |

*Primary Examiner*—Alicia M. Harrington
(74) *Attorney, Agent, or Firm*—Dalina Law Group, P.C.

(57) ABSTRACT

A fundus camera is provided with auxiliary optical components and a plurality of projected alignment marks, wherein the alignment marks are in focus and coincident on the iris of the eye when the fundus camera is correctly aligned and the auxiliary optical components allow the alignment marks to be observed as an anterior view in focus, replacing part of the view of the eye fundus which is also in focus in the same view. The auxiliary view optical components may be linked to the focus of the observation system and the associated projected focus indicating marks such that all remain in adequate focus to enable the alignment and focus of the fundus camera to be performed satisfactorily.

18 Claims, 5 Drawing Sheets

SYSTEM TO FACILITATE ALIGNMENT AND FOCUSSING OF A FUNDUS CAMERA

This application is a continuation of International Application PCT/AU02/01681, with an international filing date of Dec. 13, 2002, published in English under PCT Article 21(2), which is a Paris Convention filing of Australian Application PR 9500 having a priority date of Dec. 13, 2001. International application PCT/AU02/01681 and Australian application PR 9500 are hereby incorporated by reference herein.

BACKGROUND OF INVENTION

1. Field of the Invention

This invention relates to improvements in devices for alignment and focusing of a fundus camera.

A fundus camera is used to capture an image of the fundus (posterior portion of the eye, including the retina and blood vessels). This fundus image can be examined by a third party or compared to fundus images taken at an earlier date, to facilitate diagnosis of retinal disease.

The fundus camera comprises an objective lens to form an image of the fundus of the eye, other lenses to form an image on the recording plane of a camera, and an illumination system to project light into the eye so that the fundus image is sufficiently bright that an image may be captured on the camera.

To enable a useful image to be formed without unacceptable reflections from the anterior parts of the eye (including the cornea, iris and vitreous lens) the fundus camera must be aligned very accurately. For capture of fundus images without mydriasis to dilate the pupil, the required accuracy of the fundus camera alignment is difficult to achieve without features to guide the operator in the alignment of the fundus camera. Once correct the fundus camera alignment has been achieved, that alignment must be maintained while the camera focus is adjusted.

2. Description of the Related Art

To facilitate accurate focusing of the fundus camera, one or more lines may be projected onto the eye fundus and the reflections of these lines may then be observed through the fundus camera.

Further, split prisms may be provided within the illumination system such that the image of the projected lines on the eye fundus appears split if the camera is not correctly focused, as discussed in U.S. Pat. No. 3,925,793.

The optical components for such a system for projecting a line to aid focusing may be separate from the illumination system and combined with an afocal lens system, such that the focus of the viewing system and the focal plane of the projected line system may be maintained coincident as the focus of the viewing system is adjusted as discussed in U.S. Pat. No. 4,187,014.

If the fundus camera alignment changes during focusing, for example due to movement of the subject's eye, then the image captured may be degraded by loss of light and reflections from the anterior portion of the eye. Thus it is important that the alignment aids be available to the operator while focus is being adjusted.

Previous inventions have provided for one or more alignment marks that may be projected such that they form a single focused image in the camera system when reflected from the cornea of the eye, such as U.S. Pat. No. 4,251,139 et al.

This image may be superimposed on the image of the eye fundus, thus allowing the operator to monitor the alignment of the fundus camera while adjusting focus of the fundus image. The operation of a fundus camera incorporating such alignment marks is not intuitive and skill is required by the operator to interpret the image seen through the fundus camera to allow correct alignment of the fundus camera. Also the focus of the alignment marks may change as the focus of the fundus camera is adjusted to suit the particular subject's eye.

Alternatively, the alignment of the fundus camera can be facilitated by providing the operator with an in-focus view of the anterior portions of the eye, including the iris, during alignment. Such view has been found to not give sufficient information for accurate alignment, particularly in the axial direction, so that an additional indication of axial position of the fundus camera is desirable.

Previous inventions have provided for projection of 2 separate alignment marks onto the iris of the eye to facilitate alignment. The alignment marks may be formed by infrared light, such that the pupil of the eye does not constrict if the light enters the subject's eye. When the fundus camera is correctly positioned, the two alignment marks are coincident and in focus on the iris of the eye as discussed in U.S. Pat. Nos. 4,257,688 and 4,252,420 and 4,253,743.

Correct alignment of the fundus camera using such alignment marks has been found to be intuitive and straightforward. An observation system must be provided, however, to enable the alignment marks to be observed by the operator. This observation system may incorporate a camera system that is separate from the fundus camera optical path, but this increases the bulk of the fundus camera in proximity to the subject and the field of view of the observation system may be obscured by the subject's facial features.

To avoid these problems, the observation system may share part of the fundus camera optical path including the objective lens, by including optical components into that system so as to enable an image of the iris part of the eye to be formed. This observation system may include an infrared camera.

Previous inventions have provided for the formation of an image of anterior parts of the eye including the iris for fundus camera alignment by interposing an auxiliary lens or lenses behind the objective lens such as U.S. Pat. No. 3,936,844.

This auxiliary lens would allow the alignment marks on the iris of the eye to be observed, but does not allow the fundus of the eye to be observed concurrently.

Fundus cameras currently available that provide an anterior view option for alignment typically require the operator to manually switch the instrument from anterior view mode for alignment to fundus view mode for focusing. It is desirable that both the anterior and posterior portions of the eye are visible concurrently to facilitate intuitive, easy and accurate alignment of the fundus camera and correct focus adjustment. Also, it is desirable that focusing marks be projected near to the centre part of the fundus field of view for optimum focussing.

SUMMARY OF INVENTION

Accordingly in one form of the invention there is provided a fundus camera that enables both an eye fundus image and an anterior image to be viewed concurrently in focus, including an objective lens for forming an eye fundus image at a plane i1 at least one light source for illuminating the fundus, a reflective means for directing the or each light source onto the fundus, at least one condenser lens for directing the or each light source onto the reflecting means, an auxiliary lens disposed between said objective lens and said image plane i1 for forming an anterior image of the eye at said image plane i1, where said anterior image replaces only part of the eye fundus image formed at said image plane i1, an observation means for viewing the image formed at said image plane i1, and a photographic means for capturing said image.

Preferably, the auxiliary lens is laterally offset from an optical axis of the objective lens.

Preferably, an illumination stop is placed before the condenser lens to restrict light from impinging upon the auxiliary lens.

Preferably, the fundus camera further includes retracting means for removing said auxiliary lens and said illumination stop when a photographic image is to be captured.

The auxiliary optical components including an auxiliary lens that is placed after the objective lens and before the first image plane i1 for forming an anterior image of an anterior part of the eye at the first image plane i1. Thus an in-focus view of the anterior portion of the eye including the iris replaces part only of the eye fundus image viewed through an observation system, so that the anterior and fundus portions of the eye can be observed concurrently and in focus.

Observing the anterior and fundus portions of the eye concurrently and in focus is not possible for the typical fundus camera optical system as the entrance pupil (coplanar with the eye pupil) is relatively much smaller than the objective lens and the light from points on the fundus and anterior areas of interest traveling to the fundus camera observation system form a ray bundle of relatively small cross-section at the objective lens, with the result that eye fundus and anterior views may be separated. The auxiliary optical components also include a stop placed at a plane in the illumination system that is substantially conjugate with the plane of the auxiliary lens, to restrict light from the illumination system that may fall on the auxiliary lens and so result in excessive light being reflected from surfaces of the fundus camera or the subject's eye back into the fundus camera.

Some of the auxiliary optical components may be removed from the optical path of the fundus camera when required to enable an unobstructed image to be captured by a photographing system.

Preferably a plurality of separate alignment marks are projected onto the iris of the eye such that the alignment marks are coincident and in focus and may be observed in the anterior view when the fundus camera is correctly aligned.

It is also preferable that the auxiliary lens is offset so that the centre portion of the field of view is substantially unobscured to allow observation of the fundus and focus targets projected thereon for optimum focussing. The optical axis of the auxiliary lens may be at the centre of the auxiliary lens or may be offset relative to the centre of the auxiliary lens thereby optimizing the field of view of the anterior view so that the anterior view includes that anterior portion of the eye upon which the alignment targets are projected when the fundus camera is correctly aligned. Alternatively or in addition a wedge prism may be included with the auxiliary lens to modify the offset of the field of view of the anterior view.

Preferably in one embodiment of the invention the auxiliary lens is linked to the fundus camera focussing system by linkages or the like such that the auxiliary lens moves axially through a distance so as to maintain the anterior view in adequate focus to allow clear observation of the alignment marks as the focus state of the fundus image is adjusted by axial movement of the fundus camera focussing system through a distance not necessarily the same.

In a further form of the invention, the auxiliary components include a first mirror or first reflecting prism that is interposed behind the objective lens between the objective lens and a first image plane ii, so that part only of the light coming from the objective lens is then passed through an optical system that then forms an image of the anterior part of the subject's eye on the image plane of the observation optical system, replacing part only of the image of the fundus of the subject's eye. Said first mirror may be partly reflecting only so that a portion of light from the objective lens passes through the mirror, so that the anterior view appears superimposed over the eye fundus view at the image plane of the observation system.

The anterior portion of the eye that appears in the anterior view may be illuminated by light projected from the alignment target projection devices such that the light illuminates the anterior region around the targets, or from an external source or from partially transmitting regions of the stop that is provided in the illuminating system where such light does not reflect from the cornea of the eye so as to cause unacceptable transmission of light back into the observation system.

It is also preferable that the alignment marks are projected from non-opposite positions such that a first mark moves over the eye iris tangentially to the eye axis as the fundus camera is moved towards the eye and a second mark moves at an angle other than 180 degrees to the first, to further facilitate the perception of the operator of any misalignment of the alignment marks.

The alignment marks may be projected from a source external to the optical path of the fundus camera, or may be projected from a source internal to the fundus camera and then through the objective lens to the subject eye.

It is also preferable that the observation system includes a reticule that is concentric with the pupil of the eye when the system is correctly aligned with respect to the eye, to further facilitate correct alignment of the instrument.

It is also preferable that the projected alignment and focus marks are formed in infrared light and the observation system includes a camera sensitive to infrared light, so that projection of the marks into the subject's eye does not cause the subject's pupil to contract.

The image of the fundus of the subject eye and the anterior view of the anterior portion of the eye with alignment targets may be observed by way of an observation camera separate to the primary photographing camera. Alternatively this image may be observed by the primary photographing camera if the photographing camera is rendered sensitive to infrared light during the alignment phase by removal of some or all of the infrared filters typically provided for digital colour photographing cameras. These images may then be monitored on a PC or dedicated monitor.

BRIEF DESCRIPTION OF DRAWINGS

To assist with understanding the invention, reference will now be made to the accompanying drawings which show at least one preferred embodiment of the invention.

In the drawings.

DETAILED DESCRIPTION

Figure 1A:
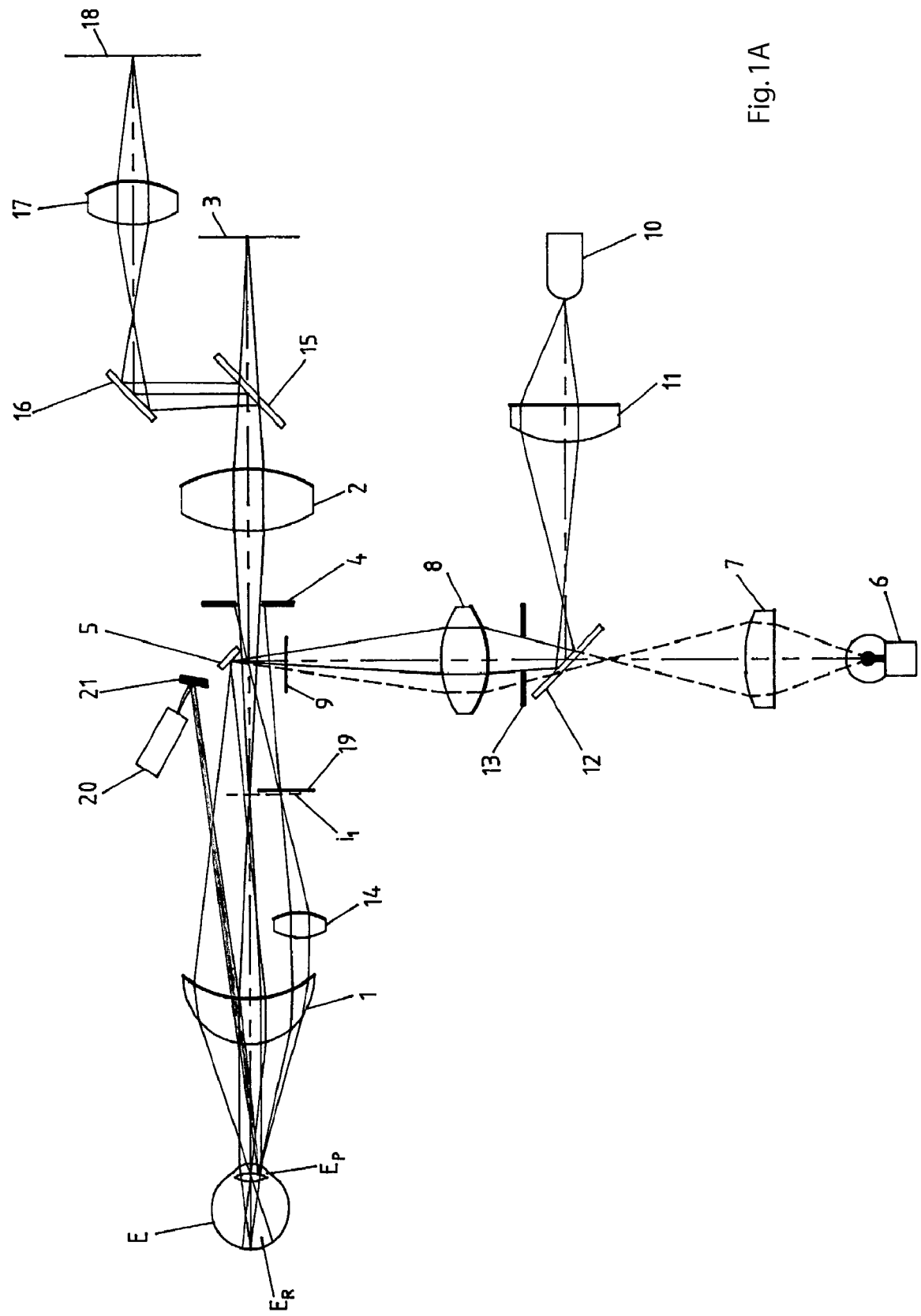
FIGS. 1A and 1B shows a preferred example of a fundus camera with projected alignment targets and viewing system according to this invention.

Referring to FIG. 1A it can be seen that the light source 10 projects light via condenser lens 11, mirror 12, lens 8, mirror 5 through objective lens 1 onto the fundus ER of the subject eye. Stop 13 is conjugate with auxiliary lens 14, such that no light from light source 10 impinges on auxiliary lens 14, thus avoiding unwanted reflections from lens 14 and also from the eye pupil EP and other anterior surfaces of the subject eye after transmission through lens 8.

Light from source 10 that is reflected from the eye fundus ER passes through objective lens 1, forming a first aerial image i1 and then to photographing lens 2, mirror 15 and 16, and relay lens 17 to the observation camera 18.

Figure 1B:
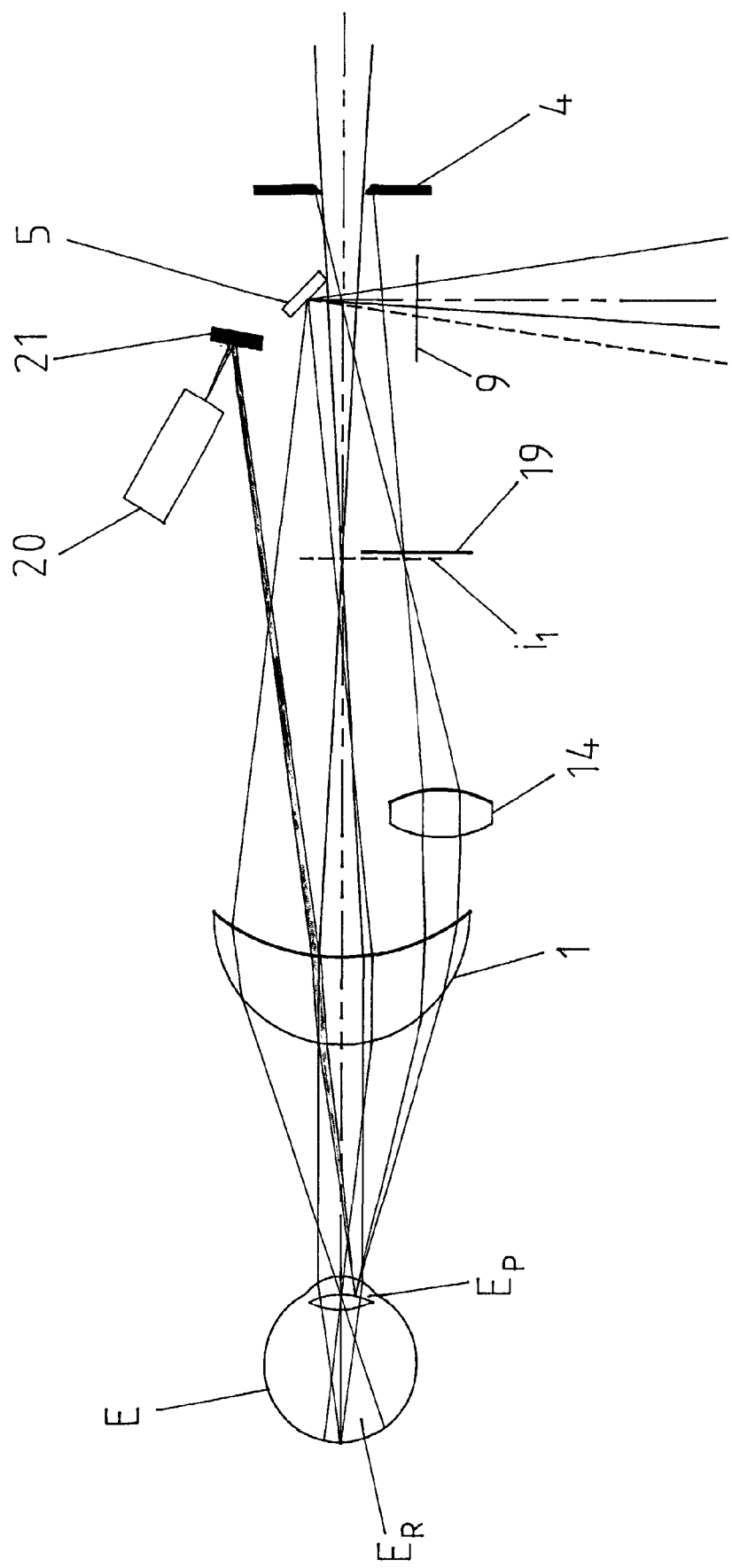

FIG. 1B shows a close up of FIG. 1A. Concurrently light from one or more alignment targets 20 is projected via mirror 21 through objective 1 and an image of the alignment target is focused onto the iris of the eye pupil EP of subject eye.

Concurrently light reflected from the eye pupil EP passes through the objective 1 and the auxiliary lens 14 to form an aerial image of the eye pupil at a first image plane i1 and then to photographing lens 2, mirror 15 and 16, and relay lens 17 to the observation camera 18. A reticule 19 may be positioned at the first image plane to provide an additional guide to aligning the fundus camera.

Figure 2:
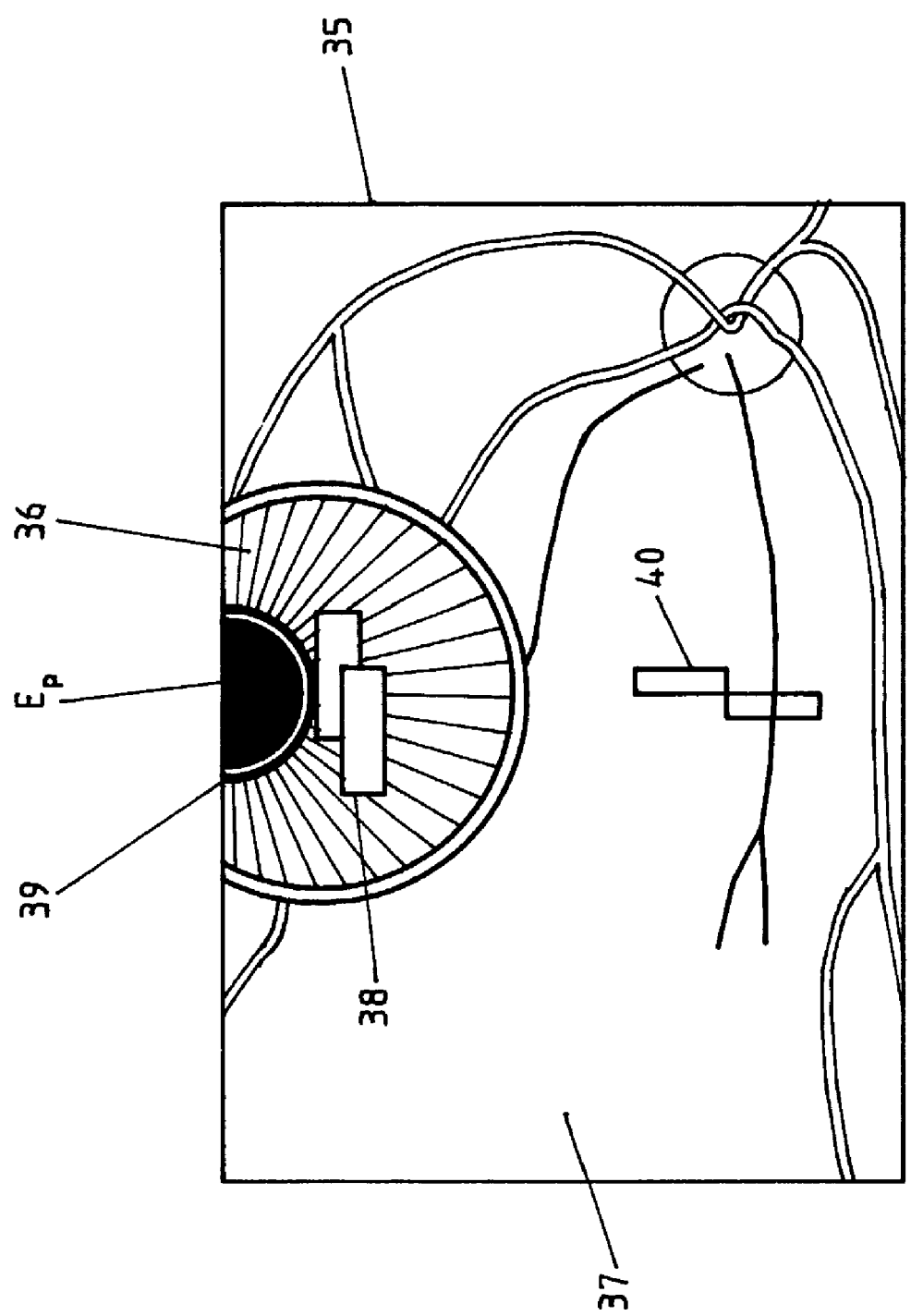
FIG. 2 shows a representation of the resultant image on the viewing system of the fundus camera.

Referring to FIG. 2, it can be seen that the image appearing on the monitoring system for the observation camera 18 comprises an image of the pupil of the eye E{ with image of the alignment target 38 on the eye iris 36 replacing part of the image of the fundus of the eye 37.

In the case of a plurality of alignment targets 20, the image of the targets 38 is comprised of a plurality of target images that are coincident or otherwise aligned when the fundus camera is correctly aligned. The reticule 19 would appear superimposed onto the image of the pupil of the eye EP as a reticule image 39, and would be concentric with that pupil when the fundus camera is correctly aligned. The split line 40 is the image of the aperture plate 24 shown in FIG. 3, and will appear as a single line when the fundus image is correctly focused.

When elements 12, 13, 14, 19, 28 and 15 are removed from the optical paths it can be seen that light projected from light source 6 now passes through lens 7 and through the optical system to the eye fundus ER of the subject eye and reflections thereof then pass through the objective lens 1 and then to the photographing camera 3, thereby enabling an unobstructed image to be captured by the photographing camera.

Figure 3:
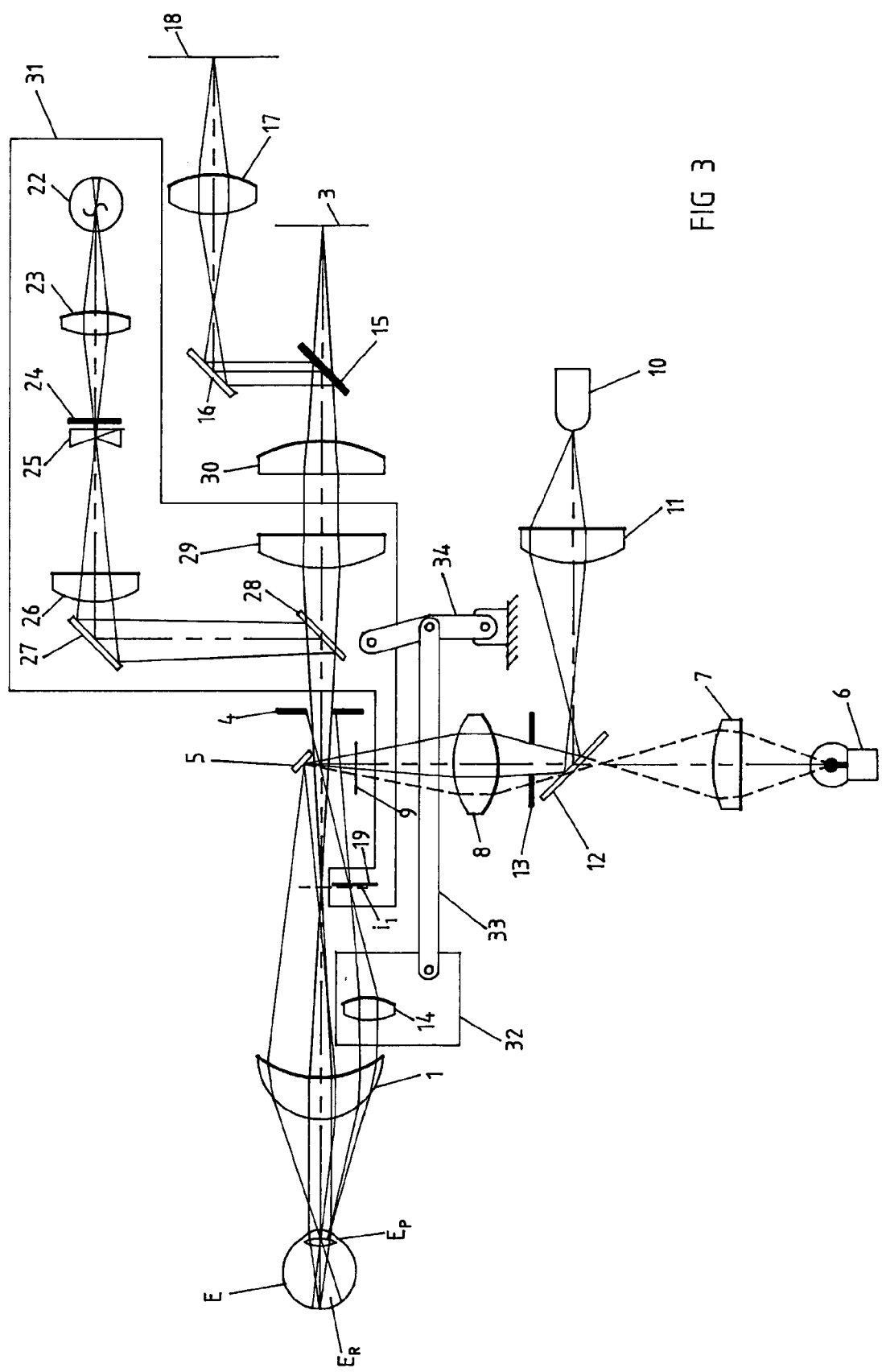
FIG. 3 shows one type of focussing system, with linkage of the auxiliary lens and reticule to said focus adjustment mechanism.

FIG. 3 shows one preferred version of the invention. Referring to FIG. 3, it can be seen that light from a source 22 can be projected through lens 23 and plate 24 that includes apertures that may be a slit or plurality of slits and then through lens 26, mirrors 27 and 28, objective 1 to the eye fundus ER. If a pair of opposed prisms 25 are placed adjacent to the aperture plate 24 then the image on the eye fundus ER will be split about a line corresponding to the junction of the two prisms if the image of the aperture is not focused exactly onto the eye fundus ER. As is well known in the art, this split target projection can be used to facilitate identification of correct focussing of the fundus camera.

Referring to FIG. 3, it can be seen that auxiliary lens 14 can be connected by a linkage to an arm 34 which is connected to a module 31 which includes items 22, 23, 24, 25, 26, 29 and 19. Module 31 can be moved to adjust the focus of the imaging system as is well known in the art, and the auxiliary lens 14 can then be seen to move in the same direction but through a different distance, so as to maintain the image of the eye pupil EP approximately coplanar with the image plane i1 defined by the focus of module 31 components.

Figure 4A:
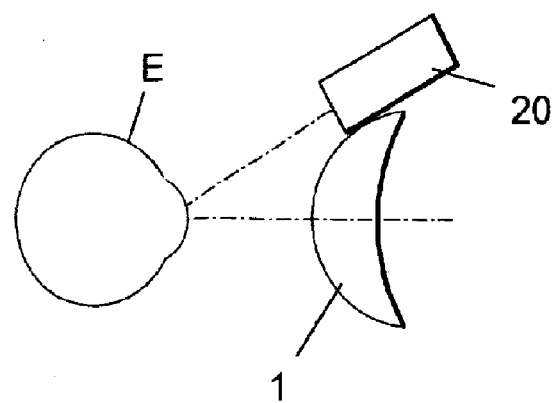
FIGS. 4A and 4B shows how perception of the movement of two alignment marks may be enhanced by projection from non-opposite positions.

Referring to FIG. 4A it can be seen that as an alternative to the design in FIG. 1, the alignment marks may be projected by means 20 external to the fundus camera optical path. In the case of either internal or external projection, the alignment marks 38 and 38' are projected such that they are coincident or otherwise aligned when the fundus camera is correctly aligned in the axial direction. Also shown schematically in FIG. 4B is the effect of the movement of the alignment marks projected onto the eye iris as the fundus camera is moved closer to the eye.

For the cases of either internal or external projection if one mark 38' is projected from projection module 20' that is in a position other than symmetrically opposite the other alignment mark projection module 20 then relative movement serves to enhance the perception of correct alignment.

Figure 4B:
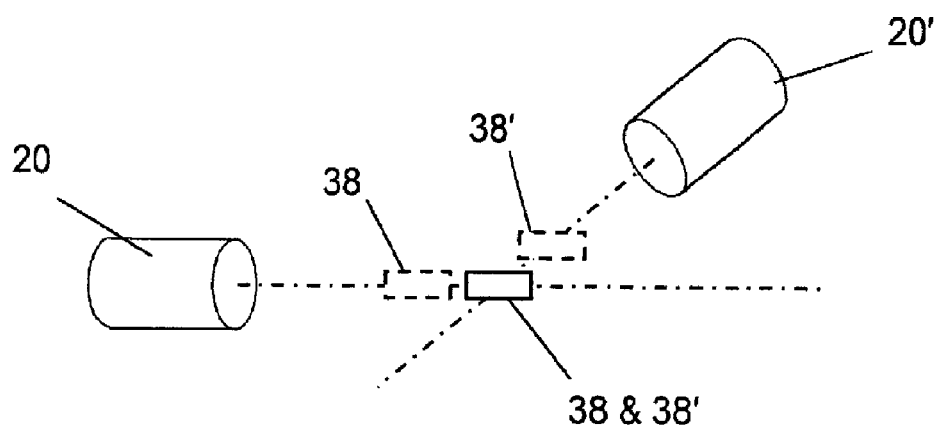

In the example shown in FIG. 4b mark 38 moves horizontally over the iris 36, as the fundus camera is moved towards the eye and the other mark 38' moves at an angle to the horizontal, to further facilitate the perception by the operator of any misalignment of the alignment marks.

Figure 5:
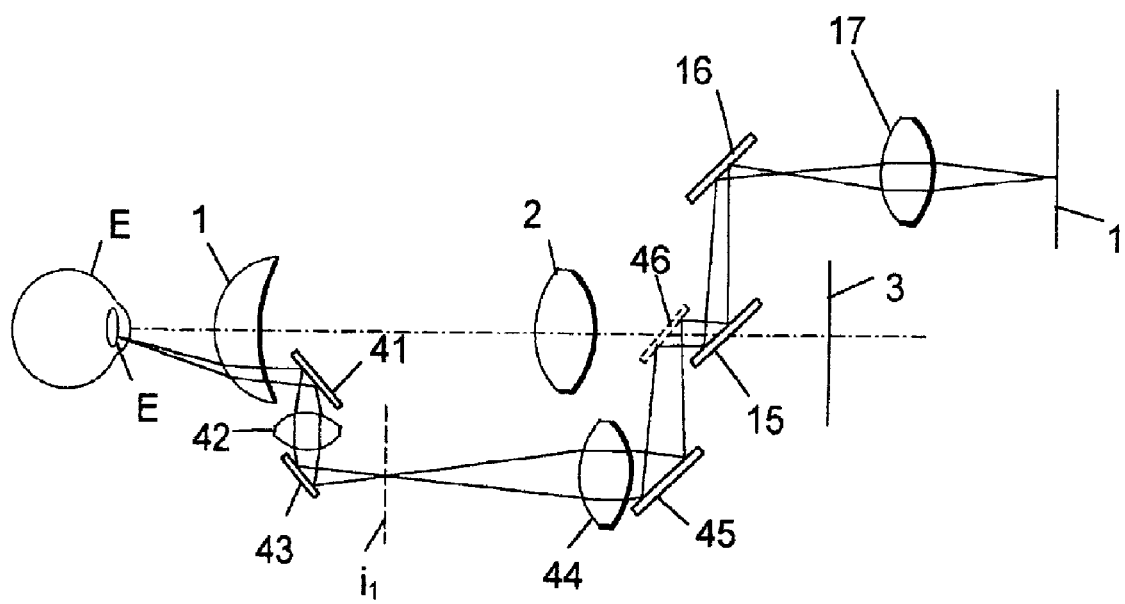
FIG. 5 shows a part of an alternative form of the invention where the anterior view image is formed in an optical path external to the fundus camera optical path.

Referring to FIG. 5 it can be seen that as an alternative to the design in FIG. 1A, the anterior view may be formed by auxiliary components that are external to the optical path of the optical system. In FIG. 5 light reflected from the eye pupil EP passes through the objective 1 and via the reflecting means 41 to the external auxiliary lens 42 to form an aerial image of a portion of the eye iris and the alignment target at a first image plane i1 and then via a second reflecting means to the external photographing lens 44, a third reflecting means 45 and a fourth partially reflecting means 46 that recombines the anterior image with the fundus image first formed at the first image plane i1.

In this embodiment of the invention items 41 and 46 are removed from the fundus camera optical path to allow an unobstructed image to be captured by the photographing camera 3.

What is claimed is:

1. A fundus camera that enables both an eye fundus image and an anterior image to be viewed concurrently in focus comprising:
    an objective lens for forming an eye fundus image at an image plane (i1);
    at least one light source for illuminating a fundus;
    a reflective means for directing said at least one light source onto said fundus;
    at least one condenser lens for directing said at least one light source onto said reflecting element;
    an auxiliary lens disposed between said objective lens and said image plane (i1) for forming an anterior image of an eye at said image plane (i1), where said anterior image replaces a portion of said eye fundus image formed at said image plane (i1);

an observation means for viewing an image formed at said image plane (i1); and, a photographic means for capturing said image.

2. The fundus camera of claim 1 wherein said auxiliary lens is laterally offset from an optical axis of said objective lens.

3. The fundus camera of claim 1 wherein at least one illumination stop is placed before said at least one condenser lens to restrict light from impinging upon said auxiliary lens.

4. The fundus camera of claim 1 further comprising retracting means for removing said auxiliary lens and said illumination stop when a photographic image is to be captured.

5. The fundus camera of claim 4 wherein said retracting means comprises a pivotally rotatable arm, rotatable to an extended position wherein said auxiliary lens is located between said objective lens and said image plane (i1) and a retracted position wherein said auxiliary lens is not located between said object lens and said image plane (i1) when said image plane (i1) is to be utilized for a photograph.

6. The fundus camera of claim 1 wherein one or more alignment marks are projected onto an iris of said eye, such that said one or more alignment marks are visible in said anterior image of said eye wherein said one or more alignment marks can be seen to be aligned when a fundus camera is correctly positioned.

7. The fundus camera of claim 6 wherein said one or more alignment marks are projected onto an iris of said eye from non opposite positions such that a first mark moves over said iris of said eye substantially parallel to a first line as a fundus camera is moved towards said eye and a second mark moves over said iris of said eye at an angle aligned other than 180 degrees to a direction of movement of said first mark along said first line.

8. The fundus camera of claim 1 wherein a first position of said auxiliary lens is coupled to a second position of a fundus camera focusing system such that said auxiliary lens moves substantially axially through a distance so as to maintain said anterior image in focus as focus of said eye fundus image is adjusted.

9. The fundus camera of claim 1 wherein said at least one light source comprises infrared light directed at said fundus of said eye and said observation means is capable of detecting infrared light.

10. The fundus camera of claim 9 wherein said at least one light source further comprises visible light.

11. The fundus camera of claim 1 wherein said photographic means comprises at least one photographic lens, a photographic plane and a photographic camera.

12. The fundus camera of claim 1 further comprising an illumination device that is located in proximity to said objective lens, such that light eminating from said illumination device illuminates an anterior region of said eye such that light does not reflect back from a cornea of said eye so as to cause unacceptable transmission of light back towards said observation means.

13. The fundus camera of claim 1 wherein said observation means includes a reticule that is concentric with a pupil of said eye when observation is correctly aligned with respect to said eye, wherein said reticule facilitates correct alignment of said photographic means.

14. The fundus camera of claim 1 wherein said observation means further comprises an observation camera separate from said photographic means.

15. The fundus camera of claim 14 wherein said image plane (i1) comprising at least one alignment target may be observed through said observation means, separate from said photographic means.

16. The fundus camera of claim 15 wherein an infrared light is used during alignment and focusing wherein said photographic means is capable of detecting infrared light during an alignment phase by removal of some or all infrared filters typically coupled to a digital colour photographic camera.

17. A method of operating a fundus camera that enables both an eye fundus image and an anterior image to be viewed concurrently in focus comprising:

inserting an auxiliary lens between an objective lens and an image plane (i1) for forming an anterior image of an eye at said image plane (i1), where said anterior image replaces a portion of an eye fundus image formed at said image plane (i1);

focusing said objective lens; and, focusing said auxiliary lens.

18. The method of claim 17 further comprising:

removing said auxiliary lens from between said objective lens and said image plane (i1); and, photographing a fundus.

* * * * *